United States Patent [19]

Puppo

[11] Patent Number: 5,230,329
[45] Date of Patent: Jul. 27, 1993

[54] LITHOTRIPTER WITH TWO LOCALIZATION DEVICES IN AN ISOCENTRIC SYSTEM

[75] Inventor: Paolo Puppo, Pieve Ligure, Italy

[73] Assignee: Medas S.p.A., Genoa, Italy

[21] Appl. No.: 739,908

[22] Filed: Aug. 2, 1991

Related U.S. Application Data

[63] Continuation-in-part of Ser. No. 433,322, Nov. 8, 1989, abandoned.

[30] Foreign Application Priority Data

Nov. 16, 1988 [IT] Italy .................. 15177 B/88

[51] Int. Cl.⁵ .............................................. A61B 17/22
[52] U.S. Cl. ................................. 128/24 EL; 378/196
[58] Field of Search ........................ 128/24 EL:660.03; 606/127, 128; 378/62, 63, 20, 196

[56] References Cited

U.S. PATENT DOCUMENTS

| | | | |
|---|---|---|---|
| 4,608,979 | 9/1986 | Beidenthal et al. | 128/24 EL |
| 4,705,026 | 11/1987 | Chaussy et al. | 128/24 EL |
| 4,936,291 | 6/1990 | Forssmann et al. | 128/660.03 |
| 4,984,565 | 1/1991 | Rattner et al. | 128/24 EL |
| 4,984,575 | 1/1991 | UchiyaMa et al. | 128/660.03 |
| 5,044,354 | 9/1991 | Goldhorn et al. | 128/24 EL |
| 5,060,650 | 10/1991 | Wurster et al. | 128/660.03 |
| 5,065,761 | 11/1991 | Pell | 128/660.03 |

FOREIGN PATENT DOCUMENTS 3503702 8/1986 Fed. Rep. of Germany ... 128/24 EL

*Primary Examiner*—Lee S. Cohen
*Assistant Examiner*—Kevin Pontius
*Attorney, Agent, or Firm*—Robert M. Wolters

[57] ABSTRACT

A lithotripter (13), and a device for the localization of calculi (11), are mounted on radially moving slides attached to the supporting ring (10). In this manner, their longitudinal axes lie in the same diametric vertical plane, and pass through the center of the supporting ring. The angular distance between the longitudinal axes of the two devices is fixed, as determined by their mounting on the ring. An echograph, with its illustrated free floating probe (19), is interfaced with a computer. The origin of the echograph coordinate system corresponds to both the center of the rotating ring, and to the calculus (16), in the patient's body (14).

2 Claims, 4 Drawing Sheets

LITHOTRIPTER WITH TWO LOCALIZATION DEVICES IN AN ISOCENTRIC SYSTEM

This application is a continuation-in-part of U.S. Ser. No. 433,322 filed Nov. 8, 1989, now abandoned.

This present invention concerns an assembled lithotripter with two localization devices for the calculi, interfaced with a computer in an isocentric system, that allows the simultaneous identification and control of the fragmentation of a calculus without the need to move the patient.

According to the present knowledge of the technique, lithotripters are machines that generate shock waves, which are focused on a calculus through a semiellipsoid reflector, causing the fragmentation of the calculus in a line of progression that begins at the surface of the shockwave entry and ends at the point of shock wave exit.

According to the present knowledge of the technique, the position of the calculus is determined with the aid of a radiological device or by echography. Subsequently, the lithotripter is used for the fragmentation.

One of the main objects of this present invention is to be able to use a lithotripter in combination with two localization devices, radiological and echographic, in real time, used individually or simultaneously, without moving the patient, by viewing either the radiology or the echography screen.

This results in maximum precision in the localization of the calculus, eliminates possible errors of the single system of localization, and allows localization of the entire spectrum of the renal and biliary calculi.

Another object of this present invention is to be able to isocentricly vary the direction of the shock waves of the lithotripter, changing its delivery angle in the desired direction, without having the calculi move from the position defined by the focus of the ellipsoid, and without the need to move the patient.

These and other objects that will appear in more detail later on, have been achieved according to the present invention, by an assembled lithotripter with two localization devices for the calculi, interfaced with a computer in an isocentric system.

For the purpose of attaining these objects described, and to achieve an isocentric system, the lithotripter and one of the localization devices for the calculi, in this particular instance the radiological device, have been mounted on radially moving slides attached to a component in the shape of a ring. In this manner, their longitudinal axes lie in the same diametric vertical plane, and pass through the center of the supporting ring. The angular distance between the longitudinal axes of the two devices is fixed, as determined by their mounting on the ring. The echograph, instead, is interfaced with a computer, in which the origin of the coordinate system corresponds to the center of the supporting ring.

Consequently, with this present invention a device is obtained which, on the whole, is far more efficient. It may also be used for other types of operations, for example endourological, or traditional diagnostic procedures, which can be performed simultaneously, without the need to move the patient.

A combination according to the present invention comprises a table for supporting a patient having a bodily calculus and lithotripter apparatus comprising radiological emitter means, radiologic target means, a lithotripter including a reflector having means for generating and focussing a shock wave on a bodily calculus, common mounting means including a ring having an axis of rotation and means mounting the ring for rotation about its own axis of rotation on which the radiologic emitter means, the radiological target means, and the lithotripter are mounted for simultaneous movement thereof, an echograph device for independent locating of a calculus in a living body, means for relatively moving the table and the ring to position a bodily calculus on the ring axis of rotation with said shock wave focussed on such bodily calculus, and means for rotating the ring a few degrees about the axis of rotation to cause the shock wave to engage such calculus from a different direction.

The combination comprises a table for supporting a patient having a bodily calculus and lithotripter apparatus comprising a lithotripter including a reflector having means for generating and focussing a shock wave on a bodily calculus, mounting means including a ring having an axis of rotation and means mounting the ring for rotation about its own axis of rotation, the lithotripter being mounted on the ring with the reflector aimed toward and focussing said shock wave on the axis of rotation, means for relatively moving the table and the ring to position a bodily calculus on the ring axis of rotation with the shock wave focussed on such bodily calculus, and means for rotating the ring a few degrees about the axis of rotation to engage such calculus from a different direction.

These and other features and advantages of the present invention will become apparent with reference to the accompanied drawings, that are enclosed only for illustrative purposes and not restrictive, in which.

In the different drawings the same numerals are used for the corresponding parts.

Figure 1:
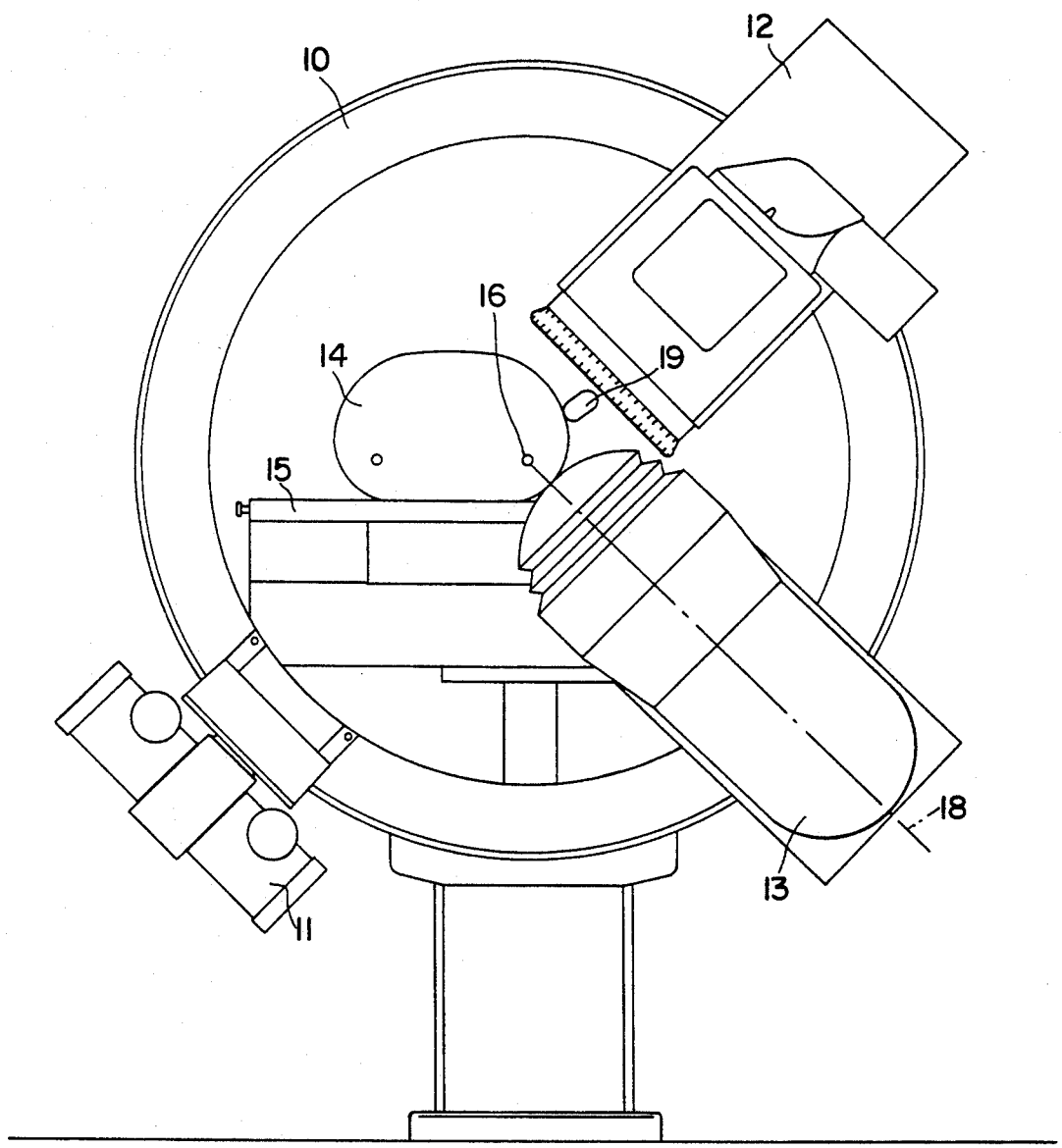
FIG. 1 illustrates a drawing of the assembly of a lithotripter with localization devices for calculi, according to the present invention.

Referring to the drawings, a radiological tube (11), is mounted on the supporting ring (10), with an associated luminance amplifier (12), which is connected to a computer not shown in the drawing. In the middle position between the radiological tube (11), and the luminance amplifier (12), a lithotripter (13) is mounted. The patient's body (14), is positioned on the bed (15), and is introduced inside the supporting ring.

Figure 2:
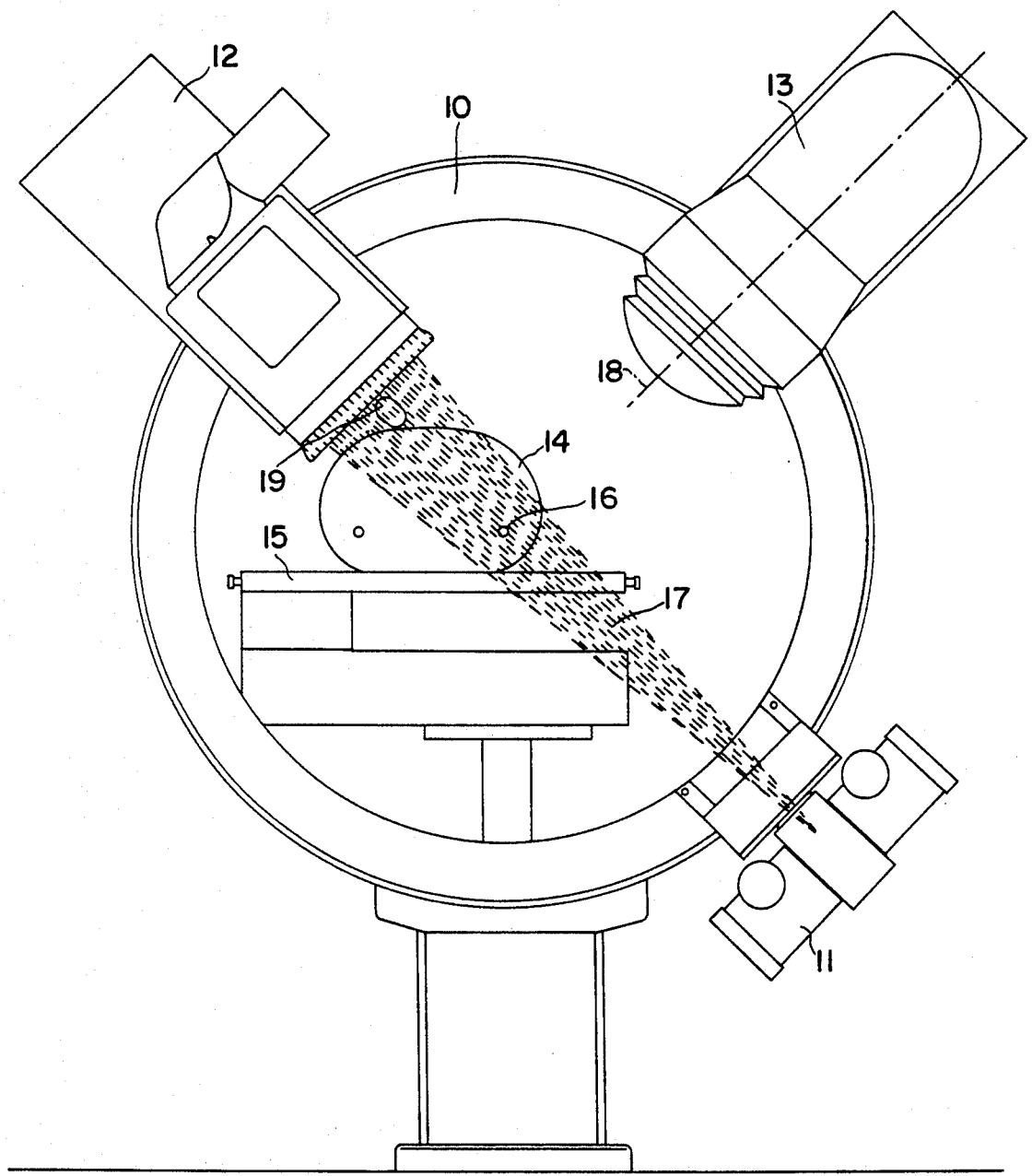
FIG. 2 illustrates an assembly of a lithotripter with localization devices for calculi according to FIG. 1, in a rotated position of 90°.

The bed (15) on which the patient's body rests and the ring (10) supporting the two components, known as the radiological tube (11) and the luminance amplifier (12), are moved until the calculus (16) is positioned exactly at the center of the supporting ring (10), and lies in the zone that is created by the rays (17), (FIG. 2).

The radiological device (11 and 12) provide the computer with the x, y, and z coordinates of the calculus to be treated.

The same coordinates can be provided by an echograph, (whose monitor is not illustrated), by means of a free floating probe (19). The echograph is connected to a computer, which calculates the position of the calculus and provides the required table position (x, y, and z as above) which will cause the position of the calculus to coincide with the center of the supporting ring (10).

The lithotripter (13), lies on the same plane as the radiological device (11 and 12), and points directly to the center of the ring (10), in which the lithotripter is mounted at a fixed angle to the direction of the ray's axis (17), and can be shifted along its own radial axis (18), to bring it as close as necessary to the patient's body (14), in order to focus the shock waves on the calculus to be fragmented (FIGS. 1 and 3), which have been identified by the computer, by radiological means, or by echographical ones. Once the calculus is positioned at the center of the device, should one verify that another solution would be preferable, with respect to the one chosen originally, and that eventually it would be more expedient to fragment the calculi with waves that originate from different directions, as illustrated in FIG. 4, the supporting ring (10), and the lithotripter (13), may be rotated to the desired position without any need to move the patient, since once localized by the current invention the calculus will always remain centered.

Figure 5:
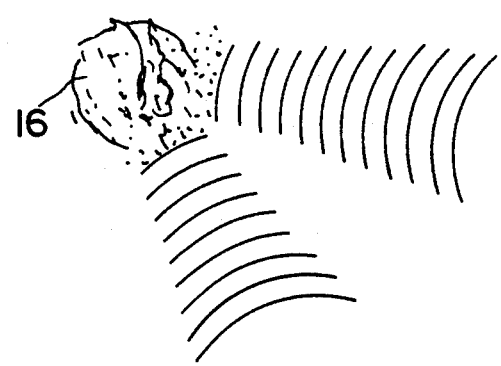
FIG. 5 illustrates how easily the calculi can be fragmented, with a lithotripter according to present invention.

This is especially useful in the case of big calculi, whose fragmentation is easier when the delivery angle of the waves comes from different directions (FIG. 5).

Figure 3:
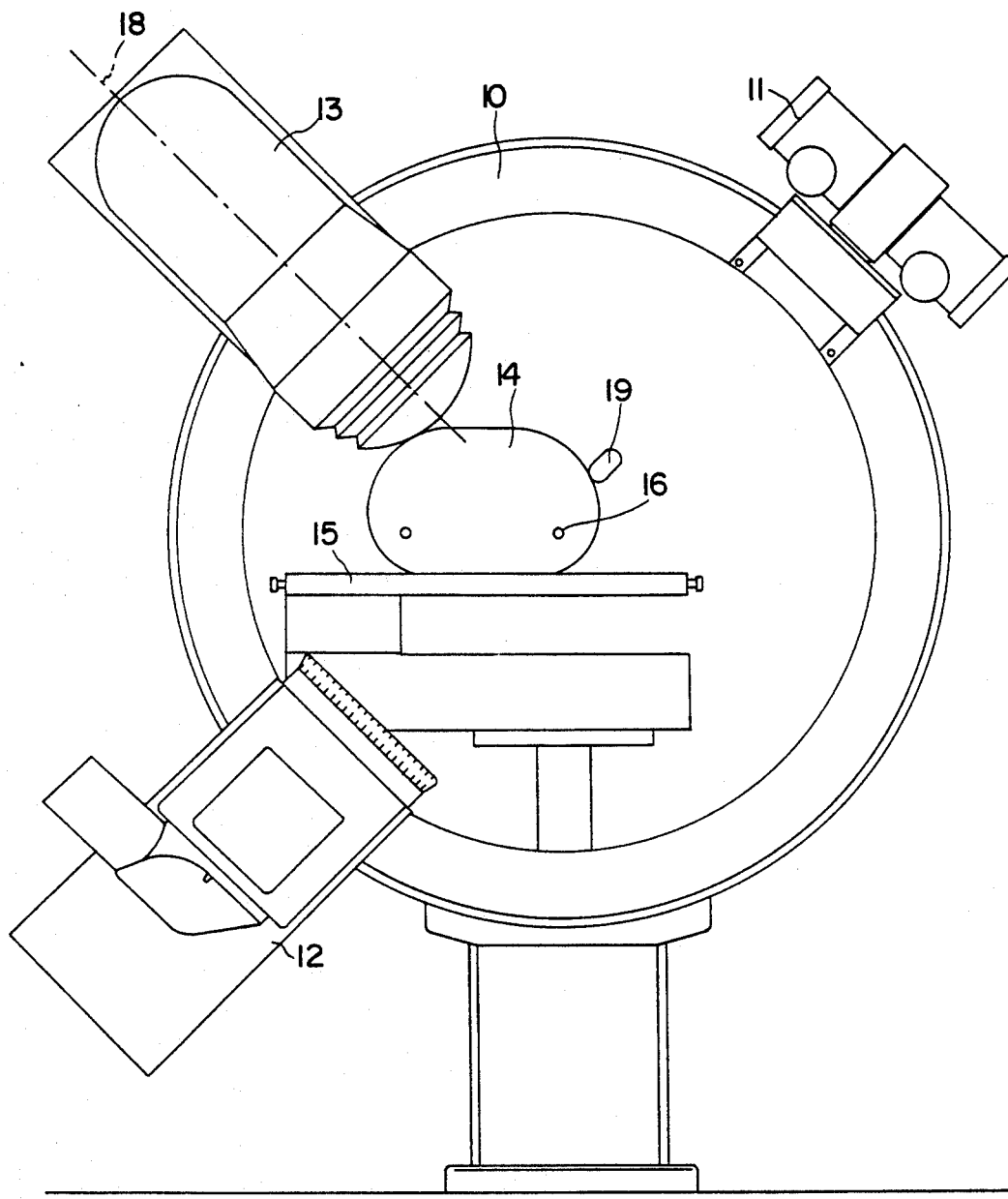
FIG. 3 illustrates an assembly of a lithotripter with localization devices for calculi according to FIG. 1, in a rotated position of 180°.
Figure 4:
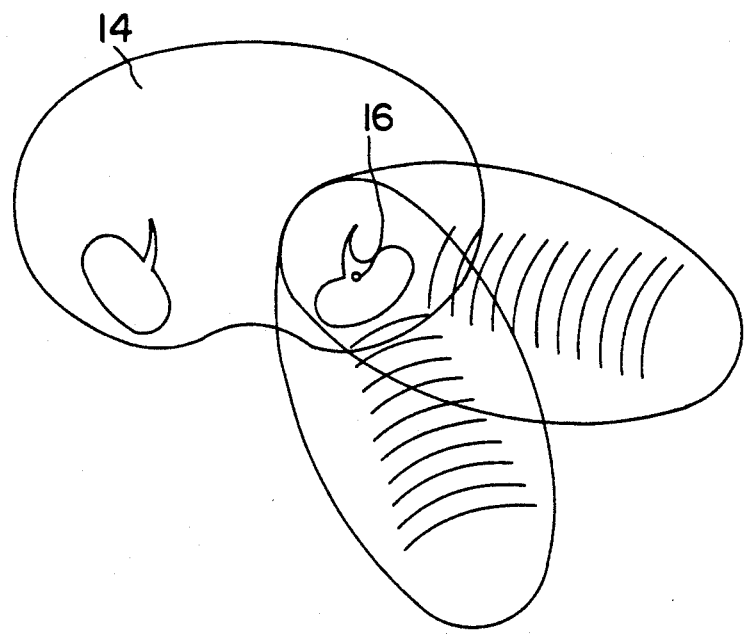
FIG. 4 is the schematic representation of how a calculus can be reached from two different directions.

FIGS. 1, 2, and 3 show three different positions of the supporting ring (10), that carry the radiological device (11), and the lithotripter (13). These drawings show various delivery angles, to illustrate the versatility of the assembly of the components according to the present invention.

The lithotripter (13) and the radiological device (11) can be simultaneously rotated in a range of approximately 260°, remaining centered on the same focus.

Maximum precision and minimal trauma to the patient results from the precise localization of the calculus, the isocentric nature of the system, and the subsequent visualization of the fragmentation process in real time. Due to the simultaneous use of the radiological and echographic devices, the isocentric system, according to the present invention, is particularly versatile, and usable for any type of localization and calculi.

In particular, and with reference to FIGS. 4 and 5, once the shock wave is focussed on the calculus, and the calculus lies on the axis of rotation of the mounting ring, the ring can be rotated a few degrees. This can be, for example, on the order of 5°-10° in either (or both) direction(s) during a shock wave treatment. No refocussing is necessary, and the shock waves engage the calculus from different directions. The diaphragm at the open end of the reflector simply slides over the skin of the patient.

Kidney stones and other bodily calculi are not of perfectly uniform construction. Consequently, there are weak spots, and the different angles (directions) from which the shock waves hit the calculus find such weak spots. Furthermore, the shock waves hit crystal planes of the calculus from different angles. This materially shortens the treatment time, by up to 60%.

According to a preferred embodiment of the invention, the size of the minor diameter, of the semiellipsoidal reflector used to focus the shock waves is greater than that of other known lithotripters, which decreases the algogenic stimuli caused by the shock waves on the skin; this is very beneficial in the range of about 30 cm.

With the lithotripter mounted on a supporting ring, maintenance and electrode changing becomes more efficient in respect to other known lithotripters due to the accessibility of the lithotripter on this present invention.

What is claimed is:

1. Lithotripter apparatus for use in combination with a table for supporting a patient having a bodily calculus and comprising a radiological emitter, radiologic target, a lithotripter having a reflector having means for generating and focusing a shock wave on a bodily calculus, said reflector having a major axis of revolution and a minor axis transverse of said major axis, common means for mounting including a substantially continuous 360° ring having a horizontal axis of rotation, said ring having a vertical diameter and a horizontal diameter through said axis of rotation, and means for supporting said ring from below and substantially symmetric about said vertical diameter and substantially below said horizontal diameter for rotation about said axis of rotation while maintaining said axis of rotation substantially horizontal, said radiological emitter, said radiological target, and said lithotripter being mounted on said ring for simultaneous movement thereof, means for moving said patient supporting table with a patient thereon having a bodily calculus relative to said ring to position such bodily calculus on said ring axis of rotation with a shock wave focused on such bodily calculus, and means for moving said ring a few degrees of rotation to cause said shock wave to engage such calculus from a different direction.

2. The combination according to claim 1 wherein said lithotripter includes an ellipsoiodal reflector having fixed major and minor axes, the minor axis having a diameter on the order of 30 cm.

* * * * *